United States Patent [19]

Olevsky

[11] 4,374,522

[45] Feb. 22, 1983

[54] TAMPON WITH CENTRAL RESERVOIR

[75] Inventor: Howard Olevsky, Appleton, WI

[73] Assignee: Kimberly-Clark Corporation, Neenah, Wis.

[21] Appl. No.: 244,070

[22] Filed: Mar. 16, 1981

[51] Int. Cl.³ .............................................. A61F 13/20
[52] U.S. Cl. .................................................... 128/285
[58] Field of Search ........................ 128/263, 270, 285

[56] References Cited

U.S. PATENT DOCUMENTS

| 1,582,201 | 4/1926 | Whittaker | 128/285 |
| 1,669,295 | 5/1928 | Hallenberg | 128/285 |
| 2,845,071 | 7/1958 | Wade | 128/285 |
| 2,926,667 | 3/1960 | Burger, Jr. et al. | 128/285 |
| 3,102,540 | 9/1963 | Bentov | 128/285 |
| 3,491,758 | 1/1970 | Mullan | 128/285 |
| 3,499,448 | 3/1970 | Jones | 128/285 |
| 3,572,341 | 3/1971 | Glassman | 128/285 |
| 4,010,751 | 3/1977 | Ring | 128/285 |

*Primary Examiner*—Rosenbaum C. Fred
*Attorney, Agent, or Firm*—Howard Olevsky; William D. Herrick

[57] ABSTRACT

A tampon having a pledget with a bullet-shaped outer configuration as provided in which the bottom portion of the tampon has a fluid impermeable layer and the inner portion of the tampon is hollow. The inner portion serves as a reservoir for excess menstrual fluid.

5 Claims, 2 Drawing Figures

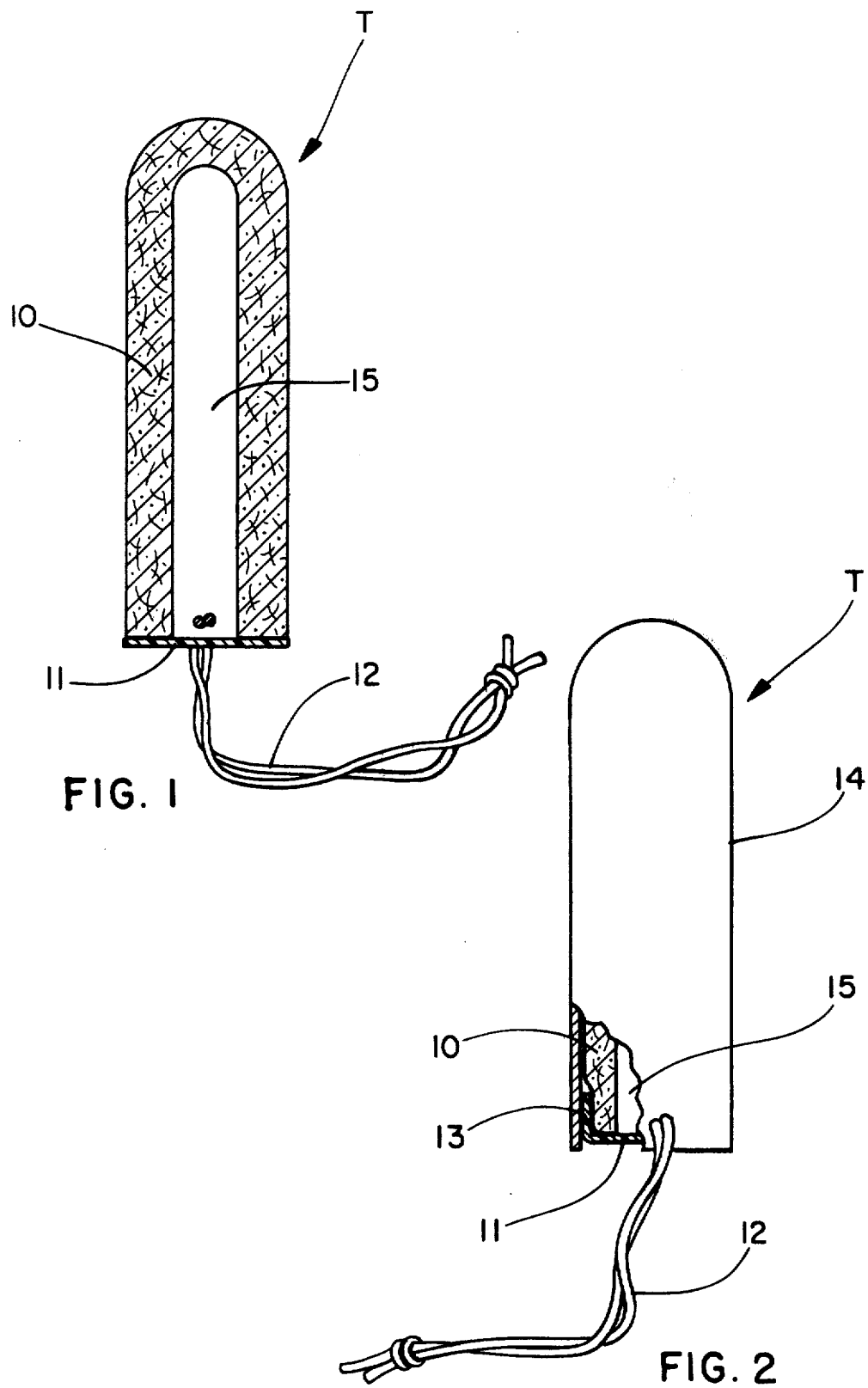

TAMPON WITH CENTRAL RESERVOIR

FIELD OF THE INVENTION

This invention relates to a tampon and particularly to a tampon having a hollow central core.

BACKGROUND OF THE INVENTION

One type of tampon commercially available at the present time is made of a compressed cellulosic fiber in an elongate bullet-shape i.e. the leading edge of the tampon pledget is arcuate while the length of the tampon extends for a distance of from about three to four inches. The tampons of this type are generally formed as layers of rectangular shaped sheets which are placed into a mold which compresses and heat sets them to form the bullet-shape. The tampon is compressed to maintain its shape and also to reduce its size to allow for easier insertion. During use the tampon absorbs fluid and swells in a manner which provides for substantial absorption at the outer portion of the tampon with only minimal uptake of fluid by the inner core. This central core area, therefore, adds little to the absorptive capacity of the tampon.

Recently a disease condition known as toxic shock syndrome has been associated with the wearing of tampons. While the disease syndrome is primarily associated with certain brands of tampons, patterns of use seem to indicate that high absorptive capacity with the concomitant extended period of wear of certain tampons are factors which contribute to the formation of this condition and also, possibly, to its severity. In other words, tampons of limited absorptive capacity requiring relatively more frequent changes may be desirable.

SUMMARY OF THIS INVENTION

According to this invention a tampon is provided which is made of conventional cellulosic materials such as rayon fibers which have been compressed into a bullet-shape with an open bottom surface sealed by a fluid impermeable sheet. The fluid impermeable bottom surface and the traditional bullet-shaped pledget defines a hollow core central reservoir area which is devoid of absorbent material. As the outer portion of the tampon is saturated, fluid flow tends to migrate into this central area. Due to the presence of the fluid impervious bottom layer the menstrual fluid will not flow downward out of the reservoir but will be maintained therein.

While this reservoir area will only hold and maintain relatively slight amounts of fluid when compared to the absorptive fibrous portion of the pledget, by providing this barrier layer as the bottom surface of the pledget, some fluid will indeed be retained.

There are several advantages readily apparent to the tampon according to this invention. First, empty space is utilized as part of the absorptive capacity thereby decreasing the amount of material needed to provide a tampon. Secondly, when the tampon is removed increased flexibility is obtained due to the presence of this hollow core area. In addition, the steps of compression and heat setting require less energy due to the reduced overall density of the tampon.

A currently preferred method of assembly of the tampon utilizes conventional layering techniques in which cellulosic fiber is formed in a rectangular pledget and placed in a mold for forming. There are two major differences in the formation of the absorptive component, however. A reduced number of layers of fiber is utilized and a male member is inserted into the bullet-shaped female member to accomplish the desired configuration.

The fluid impervious bottom portion which is added after forming is preferably fused to the bottom of the absorbent portion of the tampon but, it may also be adhesively attached. Fusing may occur during the compression setting of the tampon thereby eliminating a separate step.

This invention may be more readily understood by reference to the drawings in which:

FIG. 1 is a cross section of one embodiment of this invention and;

FIG. 2 is a second embodiment partially in cross section.

According to FIG. 1 a tampon T having a bullet-shaped outer configuration 10 of absorbent material is fused to fluid impermeable layer 11 at the base of the pledget. Withdrawal string 12 is shown extending from an opening in layer 11 and is retained by a knot placed in the upper surface of this layer. The combination of fluid impervious layer 11 and absorptive pledget 10 defines a cavity 15 which is about 20 to about 70% by volume of the tampon.

As shown in FIG. 2, a tampon similar to the embodiment shown in FIG. 1 is provided except that an outer wrap 14 surrounds the absorptive portion of the pledget 10 and the fluid impervious layer 11. In this instance, the fluid impervious layer 11 is extended up along the sides of the fluid absorptive layer 10 to form shoulder 13. This particular configuration provides a superior barrier to leakage. The utilization of the wrapper is particularly preferred when a fluid impervious layer 13 has such a shoulder to eliminate any irritation which may be associated with this layer upon removal. As can be seen also in FIG. 2, the withdrawal string 12 is affixed to the gathered portion of the outer wrap 14 rather than to the baffle itself. This is done conventionally and is well known in the prior art.

As mentioned briefly above, the fluid impervious layer 11 is preferably fused to the absorptive portion of the tampon. Fusing performs a better seal and is more rapidly accomplished. In some instances, depending upon the thickness of the tampon, it may be desirable to include fusible fibers particularly in the bottom portion of the tampon pledget to enhance the fused seal.

What is claimed is:

1. A tampon comprising a compressed bullet-shaped absorbent pledget having a tapering leading edge, a hollow central core, said pledget in fluid conductive contact with said core, a fluid impermeable layer attached to the base of the pledget to seal the central core area, and a withdrawal means attached to said impermeable layer.

2. A tampon according to claim 1 wherein the reservoir is from 20 to 70% of the volume of the pledget.

3. A tampon according to claim 1 wherein the fluid impervious layer is fused to the absorbent part of said pledget.

4. A tampon according to claim 1 wherein the fluid impervious layer extends upward from the base portion and is fused to the sides of the pledget.

5. A tampon according to claims 1, 2, 3 or 4 wherein the pledget is surrounded by a bag and a withdrawal string is attached thereto.

* * * * *